United States Patent [19]
Pruzanski et al.

[11] Patent Number: 5,523,297
[45] Date of Patent: Jun. 4, 1996

[54] INHIBITION OF EXCESSIVE PHOSPHOLIPASE $A_2$ ACTIVITY AND/OR PRODUCTION BY NON-ANTIMICROBIAL TETRACYCLINES

[75] Inventors: Waldemar Pruzanski, Toronto, Canada; Lorne M. Golub, Smithtown, N.Y.; Peter Vadas, Toronto, Canada; Robert A. Greenwald, Melville, N.Y.; Nangavarum S. Ramamurthy, Smithtown, N.Y.; Thomas F. McNamara, Port Jefferson, N.Y.

[73] Assignee: The Research Foundation of State University of New York, Albany, N.Y.

[21] Appl. No.: 426,899

[22] Filed: Apr. 21, 1995

Related U.S. Application Data

[63] Continuation-in-part of Ser. No. 115,158, Aug. 31, 1993, which is a continuation-in-part of Ser. No. 25,035, Mar. 2, 1993, abandoned.

[51] Int. Cl.$^6$ .................................................. A61K 31/65
[52] U.S. Cl. ................................................................ 514/152
[58] Field of Search ...................................................... 514/152

[56] References Cited

U.S. PATENT DOCUMENTS

| | | | |
|---|---|---|---|
| 4,666,897 | 5/1987 | Golub et al. | 514/152 |
| 4,704,383 | 11/1987 | McNamara et al. | 514/152 |
| 4,925,833 | 5/1990 | Golub et al. | 514/152 |
| 4,935,411 | 6/1990 | McNamara et al. | 514/152 |
| 4,935,412 | 6/1990 | McNamara et al. | 514/152 |
| 5,045,538 | 9/1991 | Schneider et al. | 514/152 |
| 5,258,371 | 11/1993 | Golub et al. | 514/152 |
| 5,308,839 | 5/1994 | Golub et al. | 514/152 |
| 5,459,135 | 10/1995 | Golub et al. | 514/152 |

OTHER PUBLICATIONS

Sugatani et al., "In Vitro Actions Of Some Antibiotics On Phospholipases", *J. of Antibiotics* 32: 734–739 (1979).
Pruzanski et al., " Phospholipase $A_2$—A Mediator Between Proximal And Distal Effectors Of Inflammation", *Immuno. Today* 12: 143–146 (1991).
Granström, "The Arachidonic Acid Cascade", *Inflammation* 8: S15–25 (1984, suppl 5).
O'Flaherty, "Lipid Mediators Of inflammation And Allergy", *Lab. Invest.* 47: 314–329 (1982).
Trang, "Prostaglandins And Inflammation", *Sem. Arthritis Rheum.* 9: 153–190 (1980).
Williams, "Interactions Between Prostaglandins, Leukotrienes And Other Mediators Of Inflammation", *Br. Med. Bull.* 39: 239–242 (1983).
Van den Bosch, "Intracellular Phospholipases A", *Biochem. Biophys. Acta* 604: 191–246 (1980).
Vadas et al., "Role Of Secretory Phospholipases $A_2$ In The Pathobiology Of Disease", *Lab. Invest.* 55: 391–404 (1986).
Mizel, "The Interleukins", *FASEB J.* 3: 2379–2388 (1989).
Beutler et al., "Cachectin: More Than A Tumor Necrosis Factor", *New Engl. J. Med.* 316: 379–385 (1987).
Nathan et al., "Cytokines: Interferon–γ", in *Inflammation* (Gallin et al. eds.) Raven Press 229–251 (1988).
Braquet et al., "Platelet–Activating Factor And Cellular Immune Responses", *Immunol. Today* 8: 345–352 (1987).
Marcus, "Eicosanoids: Transcellular Metabolism", in *Inflammation* (Gallin et al. eds.) Raven Press 129–137 (1988).
Wolpe et al., "Macrophage Inflammatory Proteins 1 And 2: Members Of A Novel Superfamily Of Cytokines", *FASEB J.* 3: 2565–2573 (1989).
Hsueh et al., "Two Phospholipase Pools For Prostaglandin Synthesis In Macrophages", *Nature* 290: 710–713 (1981).
Franson et al., "Isolation And Characterization Of A Phospholipase $A_2$ From An Inflammatory Exudate", *J. Lipid Res.* 19: 18–23 (1978).
Gans et al., "Extracellular Phospholipase $A_2$ Activity In Cell Free Peritoneal Lavage Fluid From Mice With Zymosan Peritonitis", *Agents & Actions* 27: 341–343 (1989).
Vadas et al., "Involvement Of Circulating Phospholipase $A_2$ In The Pathogenesis Of The Hemodynamic Changes In Endotoxin Shock", *Can. J. Physiol. Pharmacol.* 61: 561–566 (1983).
Marsh et al., "The Effects Of Honey Bee (*Apis mellifera* L.) Venom And Two Of Its Constituents, Melittin And Phospholipase $A_2$ On The Cardiovascular System Of The Rat", *Toxicon.* 18: 427–435 (1980).
Huang et al., "Relaxant Effect Of Phospholipase $A_2$ From *Vipera russelli* Snake Venom On Rat Aorta", *Eur. J. Pharmacol.* 118: 139–146 (1985).
Morgan et al., "Phospholipids, Acute Pancreatitis, And The Lungs: Effect Of Lecithinase Infusion On Pulmonary Surface Activity In Dogs", *Ann. Surg.* 167: 329–335 (1968).
Stommer et al., "Phospholipase $A_2$ Induced Diffuse Aleolar Damage—Effect Of Indomethacin And Dexamethasone Upon Morphology And Plasma–Histamine Level", *Klin. Wochenschr.* 67: 171–176 (1989).
Shaw et al., "Phospholipase $A_2$ Contamination Of Cobra Venom Factor Preparations", *Am. J. Pathol.* 91: 517–530 (1978).
Vadas et al., "Extracellular Phospholipase $A_2$ Mediates Inflammatory Hyperaemia", *Nature* 293: 583–585 (1981).
Pruzanski et al., "Inflammatory Effect Of Intradermal Administration Of Soluble Phospholipase $A_2$ In Rabbits", *J. Invest. Dermatol.* 86, 380–383 (1986).
Vadas et al., "The Proinflammatory Effect Of Intra–Articular Injection Of Soluble Human And Venom Phospholipase$A_2$", *Am. J. Pathol.* 134: 807–811 (1989).

(List continued on next page.)

*Primary Examiner*—Marianne M. Cintins
*Assistant Examiner*—William R. A. Jarvis
*Attorney, Agent, or Firm*—Hoffmann & Baron

[57] ABSTRACT

A method for treating mammals suffering from conditions associated with excess phospholipase $A_2$ activity and/or production comprising administering to the mammal an effective amount of a non-antimicrobial tetracycline sufficient to inhibit excess phospholipase $A_2$ activity and/or production is disclosed.

3 Claims, 2 Drawing Sheets

OTHER PUBLICATIONS

Vishwanath et al., "Edema–Inducing Activity Of Phospholipase $A_2$ Purified From Human Synovial Fluid And Inhibition By Aristolochic Acid", *Inflammation* 12: 549–561 (1988).

Cirino et al., "A Study Of Phospholipase $A_2$–Induced Oedema In Rat Paw", *Eur. J. Pharmacol.* 166: 505–510 (1989).

Pruzanski et al., "Phospholipase $A_2$ Activity In Sera And Synovial Fluids In Rheumatoid Arthritis And Osteoarthritis. Its Possible Role As A Proinflammatory Enzyme", *J. Rheumatol.* 12: 211–216 (1985).

Vadas et al., "Phospholipases $A_2$ In Acute Bacterial Peritonitis In Man", in *Cell Activation and Signal Initiation* (Dennis et al., eds.) Alan R. Liss 311–316 (1989).

Vadas et al., "Pathogenesis Of Hypotension In Septic Shock: Correlation Of Circulating Phospholipase $A_2$ Levels With Circulatory Collapse", *Crit. Care Med.* 16: 1–7 (1988).

Vadas, "Elevated Plasma Phospholipase $A_2$ Levels: Correlation With The Hemodynamic And Pulmonary Changes In Gram–Negative Septic Shock", *J. Lab. Clin. Med.* 104: 873–881 (1984).

Jakobsen, et al., "Demonstration Of Soluble *Plasmodium falciparum* Antigens Reactive With Limulus Amoebocyte Lysate And Polymyxin B", *Parasite Immunol.* 10: 593–606 (1988).

Clark, "Does Endotoxin Cause Both The Disease And Parasite Death In Acute Malaria And Babesiosis?", *Lancet ii:* 75–77 (1978).

Ehrlich, "Erosive Inflammatory And Primary Generalized Osteoarthritis", in *Osteoarthritis, Diagnosis, and Management* (Moskowitz et al., eds.) W. B. Saunders Co. 199–209 (1984).

Revell et al., "The Synovial Membrane In Osteoarthritis: A Histological Study Including The Characterization Of The Cellular Infiltrate Present In Inflammmatory Osteoarthritis Using Monoclonal Antibodies", *Ann. Rheum. Dis.* 47: 300–307 (1988).

Pelletier et al., "Evidence For The Involvement Of Interleukin 1 In Human Osteoarthritic Cartilage Degradation: Protective Effect Of NSAID", *J. Rheumatol.* 16: (Suppl. 18) 19–27 (1989).

Shinmei et al., "The Role Of Cytokines In Chondrocyte Mediated Cartilage Degradation", *J. Rheumatol.* 16: (Suppl. 18) 32–34 (1989).

Mitscher, "Chemical Transformations Of The Tetracycline Family", in *The Chemistry of Tetracyclines*, Chapter 6, Marcel Dekker, Publishers, N.Y. (1978).

Golub et al., "Further Evidence That Tetracyclines Inhibit Collagenase Activity In Human Crevicular Fluid And Form Other Mammalian Sources", *J. Periodont. Res.* 20: 12–23 (1985).

Golub et al., "Tetracyclines Inhibit Connective Tissue Breakdown: New Therapeutic Implications For An Old Family of Drugs", *Crit. Revs. Oral Biol. & Med.* 2: 297–322 (1991).

Golub et al., "Tetracyclines (TCs) Inhibit Matrix Metalloproteinases (MMPs): In Vivo Effects In Arthritic And Diabetic Rats, And New In Vitro Studies," *Matrix*, Suppl. No. 1: 315–316 (1992).

Sipos et al., "The Effect Of Collagenase Inhibitors On Alveolar Bone Loss Due To Periodontal Disease In Desalivated Rats," abstract presented at Matrix Metalloproteinase Conference, Destin, Florida, Sep. 11–15, (1989).

Greenwald et al. "CMT, A Metalloproteinase Inhibitor, Prevents Bone Resorption In Adjuvant Arthritis." *Arthritis Rheum.* 34 (#9 suppl): S66 (abstract #A6), abstract presented at 55th Annual Meeting, Amer. College of Rheumatology, Boston MA, Nov. 18, (1991).

Breedveld, "Suppression Of Collagen And Adjuvant Arthritis By A Tetracycline," Northeastern Regional Meeting Of The Amer. Rheum. Assoc., Atlantic City, New Jersey, Oct. 23–24, 1987.

Skinner et al., "Tetracycline In The Treatment Of Rheumatoid Arthritis", *Arthritis and Rheumatism* 14; 727–732 (1971).

Greenwald et al., "Tetracyclines Inhibit Human Synovial Collagenase In Vivo and In Vitro", *J. Rheumatol.* 14: 28–32 (1987).

Breedveld, "Minocycline Treatment For Rheumatoid Arthritis: An Open Dose Finding Study", *J. Rheumat.* 17: 43–46 (1990).

Wong et al., "Oral Ibuprofen And Tetracycline For The Treatment Of Acne Vulgaris", *Journal of American Academy of Dermatology* 11: 1076–1081 (1984).

Funt, "Oral Ibuprofen And Minocycline For The Treatment Of Resistant Acne Vulgaris", *Journal of the American Academy of Dermatology* 13: 524–525 (1985).

Vadas, et al., "Inhibition Of Synovail Fluid Phospholipase $A_2$ Activity By Two Tetracycline Derivatives, Minocycline And Coxycycline" *Arthritis and Rheumatism*, 34 Supp. 9: p. S160 (abst C167), 1983.

Greenwald, et al., "Tetracyclines Suppress Matrix Metalloproteinase Activity in Adjuvant Arthritis and in Combination With Flurbiprofen, Ameliorate Bone Damage", Journal of Rheumatology 19, 927–938 (1992).

INHIBITION OF EXCESSIVE PHOSPHOLIPASE A$_2$ ACTIVITY AND/OR PRODUCTION BY NON-ANTIMICROBIAL TETRACYCLINES

This invention was made with government support under Grant #R37-DE-03987 awarded by The National Institute of Dental Research (NIH). The government has certain rights in the invention.

BACKGROUND OF THE INVENTION

The present application is a continuation-in-part of Ser. No. 08/115,158 filed Aug. 31, 1993, which is a continuation-in-part of Ser. No. 08/025,035, filed on Mar. 2, 1993, now abandoned, both of which are incorporated herein by reference.

The present invention relates to a method of treating mammals suffering from conditions associated with excessive phospholipase A$_2$ activity and/or production by administering to the mammal an amount and/or a type of a tetracycline that is not effectively antimicrobial but which effectively inhibits excessive phospholipase A$_2$ activity and/or production. Excessive phospholipase A$_2$ activity and/or production has been implicated in several disease conditions including; rheumatoid arthritis and other tissue destructive conditions, sepsis, septic shock, multisystem organ failure, pancreatitis, malaria, psoriasis and inflammatory bowel diseases. A composition useful in the treatment of mammals suffering from conditions associated with excessive phospholipase A$_2$ activity and/or production is provided as well.

Phospholipase A$_2$ (PLA$_2$) is a ubiquitous lipolytic enzyme that has been implicated as a possible mediator of inflammation. Pruzanski et al., *Immuno. Today* 12: 143–146 (1991). Specifically, PLA$_2$ hydrolyses the 2-acyl position of glycerophospholipids, liberating free-fatty acids, mainly arachidonic acid and lysophosphatides. Granstrom, *Inflammation* 8: S15–25 (1984, suppl 5), O'Flaherty, *Lab. Invest.* 47: 314–329 (1982). Subsequently, it is believed that arachidonic acid is converted into a variety of proinflammatory eicosanoids. Trang, *Semm. Arthritis Rheum.* 9: 153–190 (1980), Williams, *Br. Med. Bull.* 39:239–242 (1983).

As indicated above, one of the suggested mechanisms of inflammation involves the activation of the arachidonic acid cascade which results in the liberation of a variety of proinflammatory eicosanoids. Van den Bosch, *Biochem. Biophys. Acta* 604: 191–246 (1980), Vadas et al., *Lab. Invest.* 55: 391–404 (1986). More recently, it has been suggested that PLA$_2$ controls the first step in the liberation of arachidonic acid from phospholipids. Vadas et al., *Lab. Invest.* 55: 391–404 (1986). It has also been suggested that the inflammatory process may be conceptualized as a four-stage event: 1) exposure to the injurious agent, 2) synthesis and release of proximal mediators, 3) synthesis and secretion of PLA$_2$ and 4) synthesis and release of distal effectors. Pruzanski et al., *Immuno. Today* 12: 143–146 (1991).

In stage 1 of this proposed scenario several factors participate in phagocytic and pinocytic activity, while others act as mediators of inflammation.

During stage 2, it is believed that a large number of proinflammatory mediators are synthesized and released in response to an injurious agent. Included in these mediators are complement, proteases, the contact activation system, toxic oxygen radicals, the interleukins (IL) (Mizel, *Faseb J.* 3: 2379–2388 (1989)); tumor necrosis factor (TNF) (Beutler et al., *New Engl. J. Med.* 316: 379–385 (1987)); interferons (INF) (Nathan et al., in *Inflammation* (Gallin et al. eds.) Raven Press 229–251 (1988)); platelet-activating factor (PAF) (Braquet et al., *Immunol Today* 8: 345–352 (1987)); eicosanoids (Marcus in *Inflammation* (Gallin et al. eds.) Raven Press 129–137 (1988)); and others (Wolpe et al., *FASEB J.* 3: 2565–2573 (1989)).

It is during stage 3 of this proposed scenario, that PLA$_2$ appears to be synthesized and secreted. At least two forms of PLA$_2$ have been found in cells. One form is associated with organelle membranes and plasmalemma and the other, a soluble form, is located in lysosomes and probably in cytosol. Hsueh et al., *Nature* 290: 710–713 (1981). The soluble form may be secreted from the cells into intravascular, interstitial or intraarticular compartments. IL-1 and TNF not only activate membrane-bound PLA$_2$ but also induce the synthesis and extracellular release of soluble PLA$_2$. Pruzanski et al., *Immunol Today* 12: 143–146 (1991).

It is believed that many disease states and conditions, which exhibit inflammation as part of the immunological process, are associated with elevated levels of PLA$_2$. Several experimental models, both in vivo and in vitro, demonstrate this possible relationship between elevated PLA$_2$ levels and inflammation. For example, glycogen-induced peritonitis in rabbits was found to be associated with high levels of soluble PLA$_2$ in peritoneal exudate fluid. Franson et al., *J. Lipid Res.* 19: 18–23 (1978). A similar PLA$_2$ was also found in the ascitic fluid of rodents after intraperitoneal injection of casein or zymosan. Gans et al., *Agents Actions* 27: 341–343 (1989). Experimental endotoxic shock is a recognized model of systemic inflammation. In rabbits challenged intravenously with *Escherichia coli* endotoxin, plasma PLA$_2$ activity rose 11-fold and correlated with the fall in mean arterial blood pressure. Vadas et al., *Can. J. Physiol. Pharmacol.* 61: 561–566 (1983). PLA$_2$s purified from the venoms of snakes or bees also produce profound hypotension in various species. Marsh et al., *Toxicon.* 18: 427–435 (1980); Huaung et al., *Eur. J. Pharmacol.* 118: 139–146 (1985). These data show that bacterial endotoxins induce the intravascular release of PLA$_2$ which in turn is related to cardiovascular collapse.

The administration of PLA$_2$ can also induce significant lung injury. This is particularly important in bacterial peritonitis and septic shock which are often complicated by acute lung injury, manifested as the adult respiratory distress syndrome (ARDS). Intravenous infusion of PLA$_2$ results in decreased compliance, impaired gas exchange, sequestration and infiltration of neutrophils in the pulmonary vascular bed and alveolar spaces. Morgan et al., *Ann. Surg.* 167: 329–335 (1968); Stommer et al., *Klin. Wochenschr.* 67: 171–176 (1989). Intratracheal instillation of PLA$_2$ induces an intense inflammatory response in rabbit lung. Shaw et al., *Am. J. Pathol.* 91: 517–530 (1978). Therefore, both circulating and locally produced endogenous PLA$_2$ may contribute to pulmonary inflammatory changes.

PLA$_2$ is also vasoactive and proinflammatory when administered by other routes. Intradermal injection of PLA$_2$ induces sustained hyperemia (Vadas et al., *Nature* 293: 583–585 (1981)); and an acute inflammatory infiltrate (Pruzanski et al., *J. Invest. Dermatol.* 86, 380–383 (1986)). Intra-articular administration of PLA$_2$ in rats causes an acute synovitis after a single injection and synovial lining cell hyperplasia after repeat injections. Vadas et al., *Am. J. Pathol.* 134: 807–811 (1989). Several studies have also documented the induction of edema in mouse and rat footpads after injection of PLA$_2$. Vishwanath et al., *Inflammation* 12: 549–561 (1988); Cirino et al., *Eur J.*

*Pharmacol.* 166: 505–510 (1989). Moreover, extracellular $PLA_2$ alters the function of phagocytes. Co-incubation of human neutrophils and monocytes with $PLA_2$ from synovial fluid results in marked superoxide generation and lysosomal enzyme release, but decreased chemotactic responsiveness.

Numerous in vivo studies have also demonstrated the possible correlation between elevated $PLA_2$ levels and inflammation. High levels of $PLA_2$ activity have been found in synovial fluid from the inflamed joints of patients with rheumatoid arthritis (RA), psoriasis and osteoarthritis. Pruzanski et al., *J. Rheumatol.* 12: 211–216 (1985). High Levels of extracellular $PLA_2$ activity are also present in patients with acute bacterial peritonitis. Vadas et al., in *Cell Activation and Signal Initiation* (Dennis et al., eds.) Alan R. Liss 311–316 (1989). Septic shock in humans is consistently associated with a marked rise in serum $PLA_2$ activity. In retrospective and prospective studies of Gram-negative septic shock, all patients had elevated serum $PLA_2$ levels during the acute hypotensive phase, which normalized during convalescence. Vadas et al., *Crit. Care Med.* 16: 1–7 (1988). In all patients, serum $PLA_2$ levels correlated directly with the magnitude and duration of circulatory collapse. Furthermore, serum $PLA_2$ was consistently elevated and the magnitude of the early increase in $PLA_2$ was prognostic of the outcome. Serum $PLA_2$ levels are also correlated with the increased risk of adult respiratory distress syndrome (ARDS) in patients with sepsis. Vadas, *J. Lab. Clin. Med.* 104: 873–881 (1984).

The exoantigens of the malaria parasite, *Plasmodium falciparum*, share common properties with endotoxin (Jakobsen, et al., *Parasite Immunol.* 10: 593–606 (1988)); and the syndrome caused by *P. falciparum* may resemble that of septic shock (Clark, *Lancet ii:* 75–77 (1978)). Serum $PLA_2$ levels are elevated as much as 1100-fold before anti-malarial therapy.

Increased levels of $PLA_2$ have also been found in patients suffering from osteoarthritis (OA). Pruzanski, et al., *J. Rheumatol.* 12: 211–216 (1985). Although OA is considered primarily a degenerative process, inflammatory episodes of varying duration are recognized as an integral part of this disease. Ehrlich, in *Osteoarthritis, Diagnosis and Management* (Moskowitz et al., eds.) W. B. Saunders Co. 199–209 (1984); Revell et al., *Ann. Rheum. Dis.* 47: 300–307 (1988). The mechanism of inflammation in OA has not been elucidated, but recently the role of inflammatory mediators has emerged as an important pathogenetic factor. Pelletier et al., *J. Rheumatol.* 16: (Suppl. 18) 19–27 (1989); Shinmei et al., *J. Rheumatol.* 16: (Suppl. 18) 32–34 (1989).

The diseases and conditions discussed above are not meant to be all encompassing. As the mechanisms of other disease processes are elucidated, $PLA_2$ may be implicated as a possible mediator of the inflammatory response in those diseases as well. What is evident is the presence of elevated $PLA_2$ levels in the inflammatory process in numerous serious diseases.

In spite of classical therapies for the treatment of the above diseases, the concomitant inflammation associated with excess levels of $PLA_2$ in these diseases remains a problem. It is apparent therefore that a need exists for therapeutic agents that inhibit the excessive activity and/or production of $PLA_2$, thereby controlling or eliminating its effect in various disease conditions. The present invention is intended to address this need.

In particular, the present inventors has discovered that the use of certain tetracyclines inhibits the excessive activity and/or production of phospholipase $A_2$ ($PLA_2$). In addition, the tetracyclines of the present invention can be combined with other classical therapeutic agents, such as anti-inflammatory agents or other medications which have been routinely used to treat the specific conditions discussed above. Other classical medications have not been known to function as inhibitors of excessive $PLA_2$ activity and/or production. In contrast to these other conventional medications, the tetracyclines of the present invention have clearly demonstrated the inhibition of excessive $PLA_2$ activity and/or production through the use of certain tetracyclines which inhibit the activity and/or production of $PLA_2$.

Tetracyclines constitute a family of well known natural and synthetic broad spectrum antibiotics. The parent compound, tetracycline, exhibits the following general structure:

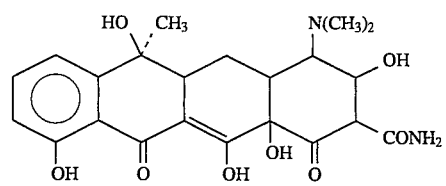

The numbering system of the ring nucleus is as follows:

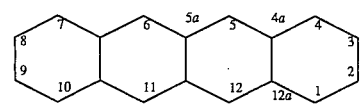

Tetracycline as well as the 5-OH (Terramycin) and 7-Cl (Aureomycin) derivatives exist in nature, and are well known antibiotics. Natural tetracyclines may be modified without losing their antibiotic properties, although certain elements of the structure must be retained. The modifications that may and may not be made to the basic tetracycline structure have been reviewed by Mitscher in *The Chemistry of Tetracyclines*, Chapter 6, Marcel Dekker, Publishers, N.Y. (1978). According to Mitscher, the substituents at positions 5–9 of the tetracycline ring system may be modified without the complete loss of antibiotic properties. Changes to the basic ring system or replacement of the substituents at positions 1–4 and 10–12, however, generally lead to synthetic tetracyclines with substantially less or effectively no antimicrobial activity. For example, 4-dedimethylaminotetracycline is commonly considered to be a non-antimicrobial tetracycline.

The use of tetracycline antibiotics, while effective, may lead to undesirable side effects. For example, the long term administration of antibiotic tetracyclines may reduce or eliminate healthy flora, such as intestinal flora, and may lead to the production of antibiotic resistant organisms or the overgrowth of opportunistic yeast and fungi.

In addition to their antibiotic properties, tetracyclines have been described for a number of uses. For example, tetracyclines are also known to inhibit the activity of collagen destructive enzymes such as mammalian collagenase, gelatinase, macrophage elastase and bacterial collagenase. Golub et al., *J. Periodont. Res.* 20: 12–23 (1985); Golub et al., *Crit. Revs. Oral Biol. Med.* 2: 297–322 (1991).

Tetracyclines, administered at both antimicrobial levels and non-antimicrobial levels, have been known to play a role in reducing collagenase and other collagenolytic enzyme activity as well as collagen breakdown. U.S. Pat. Nos. 4,666,897; 4,704,383; 4,935,411; 4,935,412. In addition, tetracyclines have been known to inhibit wasting and protein degradation of mammalian skeletal muscle, U.S. Pat. No.

5,045,538. In addition, tetracyclines have been demonstrated to enhance bone formation in osteoporosis, U.S. Pat. No. 4,925,833. We have now discovered that tetracycline exhibits an anti-phospholipase $A_2$ activity.

U.S. Pat. No. 4,704,383 to McNamara et al. discloses that tetracyclines having substantially no effective antimicrobial activity inhibit collagenolytic enzyme activity in rats. McNamara et al. also report that non-antimicrobial tetracyclines reduce bone resorption in organ culture. Earlier, U.S. Pat. No. 4,666,897 to Golub, et al. disclosed that tetracyclines in general, including commercially-available antimicrobial forms of the drug, inhibit excessive mammalian collagenolytic enzyme activity resulting in decreased connective tissue breakdown including that which occurs during bone resorption.

There have been a number of suggestions that tetracyclines, including non-antimicrobial tetracyclines, are effective in treating arthritis in rats. See, for example, Golub et al., "Tetracyclines (TCs) Inhibit Matrix Metalloproteinases (MMPs): In Vivo Effects In Arthritic And Diabetic Rats, And New In Vitro Studies," *Matrix*, Suppl. No 1: 315–316 (1992); Greenwald et al. "CMT, A Metalloproteinase Inhibitor, Prevents Bone Resorption In Adjuvant Arthritis." *Arthritis Rheum.* 34 (#9 suppl): S66 (abstract #A6), abstract presented at 55th Annual Meeting, Amer. College of Rheumatology, Boston Mass., Nov. 18, 1991; Breedveld, "Suppression Of Collagen And Adjuvant Arthritis By A Tetracycline," Northeastern Regional Meeting Of The Amer. Rheum. Assoc., Atlantic City, N.J., Oct. 23–24, 1987. For a related commentary regarding the effect of non-antimicrobial tetracyclines on bone loss see Sipos et al., "The Effect Of Collagenase Inhibitors On Alveolar Bone Loss Due To Periodontal Disease In Desalivated Rats," abstract presented at Matrix Metalloproteinase Conference, Destin, Fla., Sep. 11–15, 1989.

The effect of tetracyclines has not been firmly established for human patients with rheumatoid arthritis and various studies have indicated contrary results. Thus, Skinner et al., *Arthritis and Rheumatism* 14; 727–732 (1971), reported no significant benefit from tetracycline therapy for human sufferers of rheumatoid arthritis even though Greenwald et al., reported in *J. Rheumatol.* 14: 28–32 (1987) that the oral administration of a tetracycline (minocycline) to humans with severe rheumatoid arthritis decreased the collagenase activity in the joint tissues. More recently, however, Breedveld *J. Rheumat.* 17: 43 (1990) administered to humans, with rheumatoid arthritis, minocycline over a 16 week time period and reported a statistically significant improvement in a number of parameters of this disease, e.g. grip strength, erythrocyte sedimentation rate, etc. However, this study was not a placebo-controlled double blind study.

The use of tetracyclines in combination with non-steroidal anti-inflammatory agents has been studied in the treatment of inflammatory skin disorders caused by acne vulgaris. Wong et al., *Journal of American Academy of Dermatology* 11: 1076–1081 (1984), studied the combination of tetracycline and ibuprofen and reported that tetracycline was an effective agent against acne vulgaris, while ibuprofen was useful in reducing the resulting inflammation by inhibition of cyclooxygenase. Funt, *Journal of the American Academy of Dermatology* 13: 524–525 (1985), disclosed similar results by combining anti-microbial doses of minocycline and ibuprofen.

Based on the foregoing, tetracyclines, including their chemically modified analogs, have been found to be effective in different treatments. However, there has been no suggestion or indication that chemically modified tetracyclines inhibit excessive $PLA_2$ activity and/or production.

The present invention is intended to provide a means for inhibiting the excessive $PLA_2$ activity and/or production associated with many disease states. The present invention demonstrates that chemically modified analogs of tetracycline, which have lost their antimicrobial efficacy, have a novel new use, that is, the ability to inhibit excessive $PLA_2$ activity and/or production. This non-antimicrobial property of tetracyclines reduces the severe inflammatory complications associated with excessive $PLA_2$ activity and/or production present in many disease states.

SUMMARY OF THE INVENTION

The present invention provides a method for treating mammals suffering from conditions associated with excess phospholipase $A_2$ activity and/or production which includes administering to the mammal an amount and/or type of a tetracycline which inhibits the excess $PLA_2$ activity and/or production but which is non-antimicrobial. Non-limiting examples of conditions or diseases associated with excess $PLA_2$ activity and/or production include rheumatoid arthritis, other tissue-destructive conditions, sepsis, septic shock, pancreatitis, malaria, psoriasis, inflammatory bowel diseases and multisystem organ failure among others.

Chemically-modified non-antimicrobial tetracyclines, for example dedimethylaminotetracyclines are useful in the present invention. Dedimethylaminotetracyclines include 4-dedimethylaminotetracycline, 4-dedimethylamino- 5-oxytetracycline, 4-dedimethylamino-7-chlorotetracycline, 4-hydroxy-4-dedimethylaminotetracycline, 5a,6-anhydro-4-hydroxy-4-dedimethylaminotetracycline, 6α-deoxy- 5-hydroxy-4-dedimethylaminotetracycline, 6-demethyl-6-deoxy-4-dedimethylaminotetracycline, 4-dedimethylamino- 12a-deoxytetracycline, 4-dedimethylamino- 11-hydroxy-12a-deoxytetracycline and 4-dedimethylamino-7-dimethylaminotetracycline.

Further examples of chemically-modified tetracyclines useful in the present invention are 6a-benzylthiomethylenetetracycline, the 2-nitrilo analogs of tetracycline, the mono-N-alkylated amide of tetracycline, 6-fluoro-6-demethyltetracycline, 11a-chlorotetracycline and 12a-deoxytetracycline and its derivatives. The tetracyclines may be coupled with a pharmaceutically acceptable carrier.

The present invention also provides a method for treating mammals suffering from conditions associated with excess phospholipase $A_2$ activity and/or production which includes the administration to the mammal of (i) an amount and/or type of a tetracycline that effectively inhibits excess $PLA_2$ activity and/or production and (ii) an amount of a classical therapeutic agent which, when combined with the effectively anti-$PLA_2$ amount and/or type of tetracycline, results in a significant reduction in tissue destruction.

The invention further provides a pharmaceutical composition for treating mammals suffering from conditions associated with excess phospholipase $A_2$ activity and/or production which includes a) an amount and/or type of a tetracycline that effectively inhibits $PLA_2$ activity and/or production and b) a classical therapeutic agent which, when combined with the effectively anti-phospholipase $A_2$ amount of tetracycline, results in a significant reduction in tissue destruction.

DETAILED DESCRIPTION OF THE INVENTION

Figure 1:
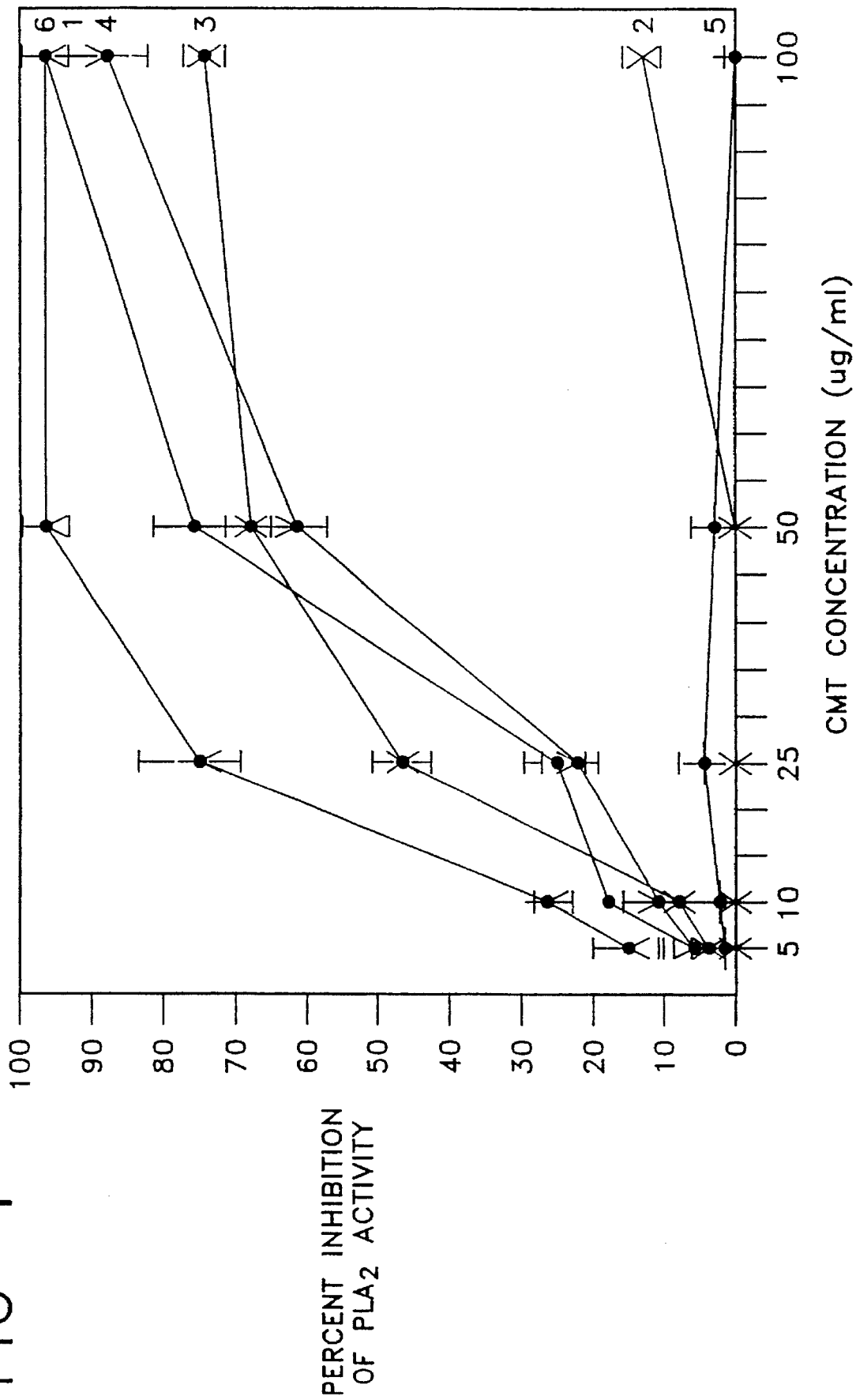
FIG. 1 is a graphic representation of assay measurements demonstrating the inhibition of recombinant human $PLA_2$ by the inventive tetracyclines as compared to those which show little or no $PLA_2$ inhibition.

It has been discovered that the use of certain tetracyclines inhibits the activity and/or production of $PLA_2$. While not wishing to be bound by any one theory, it is believed that the tetracyclines of the present invention bind to $PLA_2$ in such a way as to inhibit $PLA_2$'s ability to bind to its substrate. Alternatively, the tetracyclines of the present invention may bind to the $PLA_2$ substrate is such a way as to inhibit the substrate's ability to bind to $PLA_2$. As previously mentioned, conditions associated with excess $PLA_2$ activity and/or production which are treated in accordance with the present invention include (but are not limited to) rheumatoid and other inflammatory arthritides, other tissue-destructive conditions, sepsis, septic shock, pancreatitis, malaria, psoriasis, inflammatory bowel diseases and multisystem organ failure. Tissue destructive conditions may include Behcet's syndrome, Reiter's syndrome, Kawasaki disease, osteoarthritis and psoriatic conditions. The conditions treated by the present invention occur in mammals. Mammals include, for example, humans and laboratory animals such as rabbits, mice and rats.

The tetracyclines of the present invention can be combined with classical therapeutic agents. While the tetracycline inhibits excess $PLA_2$ activity and/or production, the classical therapeutic agent ameliorates the disease or condition through a separate mode of action.

The tetracyclines of the present invention are administered in an amount sufficient to effectuate the inhibition of $PLA_2$ activity and/or production. The amount of tetracycline used in the present invention is that which is effectively non-antimicrobial in the patient. Thus, tetracyclines generally used for their antimicrobial properties can also be used herein in doses which are effectively non-antimicrobial.

A classical therapeutic agent is a medication, treatment or therapy that is considered the standard course of action or is the medication, treatment or therapy of choice when treating a particular condition. For example, anti-inflammatory agents are routinely used in the treatment of rheumatoid arthritis and other tissue-destructive conditions.

The tetracyclines useful in the present invention may be any tetracycline administered to a mammal in a dose that is effectively non-antimicrobial in the mammal. Preferably, the tetracycline is modified so as to reduce its antimicrobial properties. Methods for reducing the antimicrobial properties of a tetracycline are disclosed in "The Chemistry of the Tetracyclines", Chapter 6, Mitscher, Marcel Dekker, Publishers, N.Y. (1978) at page 211. As pointed out by Mitscher, modification at positions 1, 2, 3, 4, 10 and 12a lead to loss of antimicrobial bioactivity. Non-antimicrobial tetracyclines are preferred since they can be used at therapeutic levels which impart fewer side effects than antimicrobial tetracyclines at the same dosage level.

The preferred tetracyclines are those that lack the dimethylamino group at position 4. Such chemically modified tetracyclines include, for example, 4-dedimethylaminotetracycline, 4-dedimethylamino-5-oxytetracycline, 4-dedimethylamino-7-chlorotetracycline, 4-hydroxy-4-dedimethylaminotetracycline, 5a,6-anhydro-4-hydroxy-4-dedimethylaminotetracycline, 6-demethyl-6-deoxy-4-dedimethylaminotetracycline, 4-dedimethylamino-11-hydroxy-12a-deoxytetracycline, 6α-deoxy-5-hydroxy-4-dedimethylaminotetracycline, 4-dedimethylamino-7-dimethylaminotetracycline, 4-dedimethylamino-12a-deoxytetracycline and its derivatives. Tetracyclines altered at the 2 carbon position to produce a nitrile, e.g., tetracyclinonitrile may be useful as non-antimicrobial agents exhibiting anti-$PLA_2$ activity when administered via non-oral routes.

Further examples of tetracyclines modified for reduced antimicrobial activity include 6a-benzylthiomethylenetetracycline, the mono-N-alkylated amide of tetracycline, 6-fluoro-6-demethyltetracycline, 11a-chlorotetracycline and 12a-deoxytetracycline and its derivatives. However, the pyrazole derivative of tetracycline is inactive.

The effective amount of tetracycline is that which is effectively anti-$PLA_2$ while not effectively antimicrobial. For purposes of this invention, a tetracycline is effectively anti-$PLA_2$ if it is present in an amount which significantly reduces excess $PLA_2$ activity and/or production. For purposes of the present invention, excess $PLA_2$ activity and/or production is defined as that which induces local or systemic inflammation and or connective tissue breakdown.

A tetracycline is considered effectively non-antimicrobial if it does not significantly prevent the growth of microbes. This of course may vary depending upon a number of factors, such as, type of tetracycline, disease state and type of microbe. The maximal useful dosage for humans is the highest dosage that does not cause adverse side effects. For the purpose of the present invention, side effects include clinically significant antimicrobial activity, as well as toxic effects. For example, a dose in excess of about 50 mg/kg/day would likely produce side effects in most mammals, including humans.

The preferred pharmaceutical composition for use in the present invention comprises a combination of the tetracycline and a classical therapeutic agent in a suitable pharmaceutical carrier. The means of delivery of the pharmaceutical carrier with the active agent may be in a variety of forms including capsules, compressed tablets, pills, solutions or suspensions. It is contemplated that carriers be included which are suitable for administration orally, topically, by injection and by other selected means.

EXAMPLES

The following Example serves to provide further appreciation of the invention but is not meant in any way to restrict the effective scope of the invention.

Example 1

Six different chemically-modified tetracyclines, including CMT-1 (4-dedimethylaminotetracycline), CMT-2 (tetracyclinonitrile), CMT-3 (6-demethyl-6-deoxy-4-dedimethylaminotetracycline), CMT-4 (4-de-dimethylamino-7-chlorotetracycline), CMT-5 (pyrazole analog) and CMT-6 (4-hydroxy-4-dedimethylaminotetracycline), were examined for their ability to inhibit $PLA_2$ activity in vitro. The sources of $PLA_2$ that were tested included recombinant human $PLA_2$, human pancreatic and porcine pancreatic $PLA_2$ and Naja naja $PLA_2$. The CMTs were dissolved in water and NaOH and the pH was subsequently reduced to pH 7.3–7.6 by the addition of acid. Various concentrations of CMTs, ranging from 5–100 µg/ml, were preincubated with the different PLA$_2$ enzymes for 30 minutes and the mixture was tested for PLA$_2$ activity using a known *E. coli* assay method (see *Arthritis and Rheumatism*, 34 Supp. 9: p. S160 (abst C167)).

Results

FIG. 1 is a graphic representation of the assay data for the different CMTs which were incubated with recombinant human PLA$_2$. At a final concentration of 5 and 10 μg/ml, none of the CMTs tested (CMTs 1–6) showed substantial inhibition of PLA$_2$ activity. At concentrations of 25 μg/ml or greater, CMT-1, CMT-3, CMT- 4 and CMT-6 all exhibited significant PLA$_2$-inhibitory activity. However, even at the highest concentrations tested, CMT-2 and CMT-5 lacked any PLA$_2$-inhibitory activity.

Therefore, selected CMT's, not all members of this category of drugs, inhibit PLA$_2$ activity in vitro.

Table 1 lists the IC$_{50}$ of the various CMTs. The IC$_{50}$, is the concentration of the drug (CMT) required to inhibit 50% of the enzyme being tested (PLA$_2$).

TABLE 1

| Drug | IC$_{50}$ |
|---|---|
| CMT-1 | 37 μg/ml |
| CMT-3 | 28 μg/ml |
| CMT-4 | 42 μg/ml |
| CMT-6 | 17 μg/ml |

It should be noted that CMT-1, 3, 4 and 6 also were found to inhibit human pancreatic and porcine pancreatic PLA$_2$.

Example 2

A chemically-modified tetracycline, 4-dedimethylamino-7-dimethylaminotetracycline (CMT-10), was examined for its ability to inhibit PLA$_2$ activity in vitro. The sources of PLA$_2$ that were tested included were recombinant human PLA$_2$ (snpPLA$_2$), human pancreatic and porcine pancreatic PLA$_2$ and Naja naja PLA$_2$. CMT-10 was dissolved in water and NaOH and the pH was subsequently reduced to pH 7.3–7.6 by the addition of acid. Various concentrations of CMT-10, ranging from 5–100 μg/ml, were preincubated with the different PLA$_2$ enzymes for 30 minutes and the mixture was tested for PLA$_2$ activity using a known *E. coli* assay method (see *Arthritis and Rheumatism*, 34 Supp. 9: p. S160 (abst C167)).

In particular, [$^{14}$C]Oleic acid-labelled *Escherichia coli* (strain K12 C600) were used as the substrate. This substrate has been characterized with respect to phospholipid composition and distribution of radiolabel. Reaction mixtures contained 10 mg bovine serum albumin, 2 mM CaCl$_2$, 2.8×10$^8$ radiolabelled *E. coli* and 0.1M Tris-HCl buffer, pH 7.5 in a total volume of 1.5 ml. Reaction mixtures were incubated at 37° C. for 30 min. The reaction was terminated by filtration through a 0.45 μm Millipore filter, thereby retaining unhydrolysed *E. coli* membranes, and allowing the [$^{14}$C]oleic acid bound to the BSA carrier, released as a result of PLA$_2$ hydrolysis, to pass through the filter. Assays were performed in duplicate and values shown represent the mean of two determinations with a SD<5% of the mean. Assays were performed in substrate excess and enzyme activities were corrected for non-enzymatic hydrolysis. One unit of PLA$_2$ activity is defined as the hydrolysis of 56 pmol of phospholipid substrate (representing 1% of total *E. coli* phospholipid) in 30 min at 37° C.

Results

Figure 2:
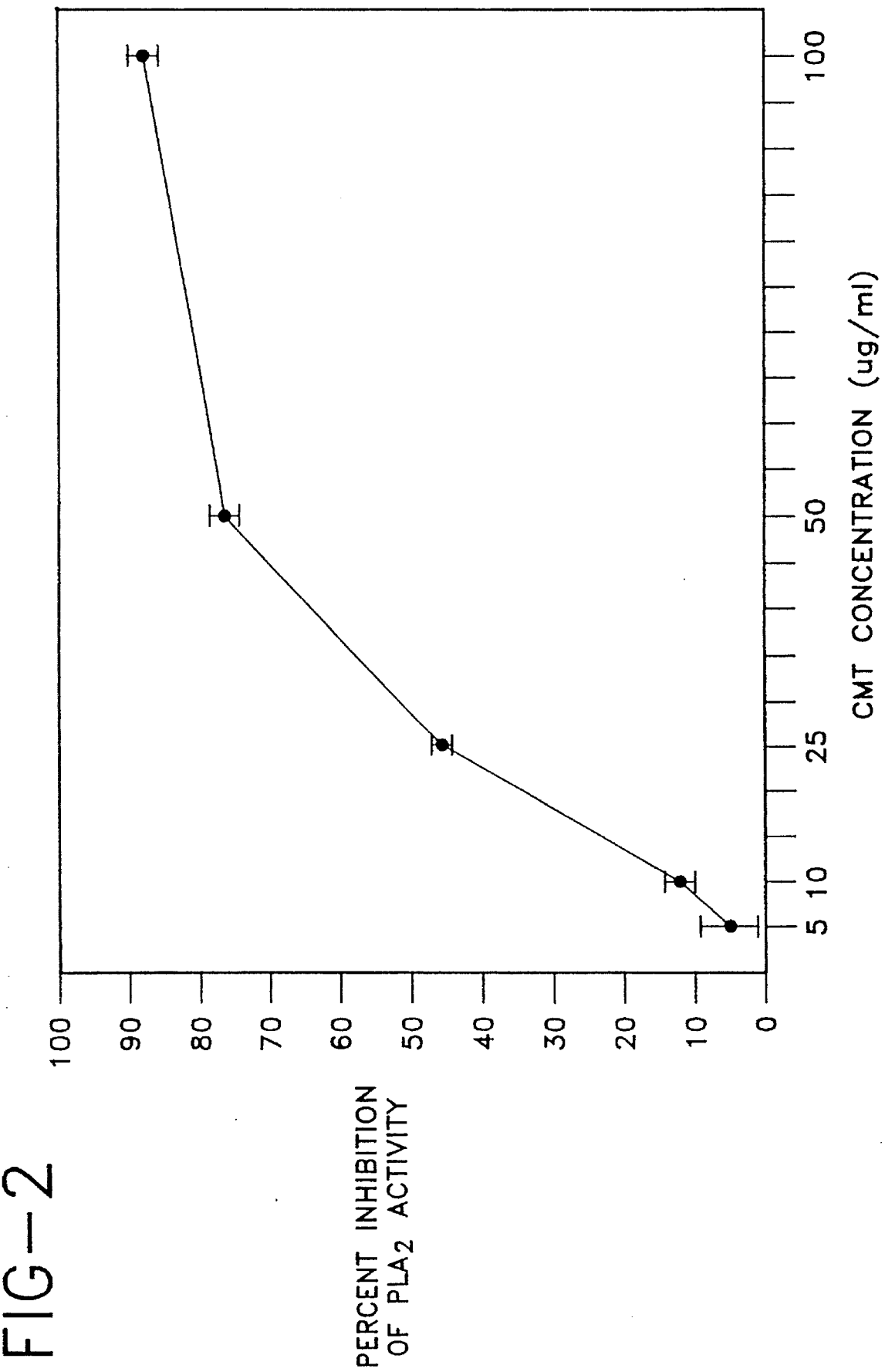
FIG. 2 is a graphic representation of assay measurements demonstrating the inhibition of recombinant human $PLA_2$ by 4-dedimethylamino-7-dimethylaminotetracycline(CMT-10).

FIG. 2 is a graphic representation of the assay data for 4-dedimethylamino-7-dimethylaminotetracycline (CMT-10) which was incubated with recombinant human PLA$_2$. At a final concentration of 5 and 10 μg/ml, CMT-10 did not exhibit substantial inhibition of PLA$_2$ activity. At concentrations of 25 μg/ml or greater, CMT-10, exhibited significant PLA$_2$-inhibitory activity. Table 2 is a tabular representation of the information found in FIG. 2.

TABLE 2

INHIBITION OF RECOMBINANT HUMAN snpPLA$_2$ BY CMT-10

| CONCENTRATION OF CMT-10 (μg/ml) | % OF INHIBITION |
|---|---|
| 5 | 4 ± 4 |
| 10 | 12 ± 2 |
| 25 | 45 ± 1 |
| 50 | 75 ± 2 |
| 100 | 87 ± 2 |

The IC$_{50}$ of CMT-10 is 30 μg/ml. The IC$_{50}$, is the concentration of the drug, CMT-10, required to inhibit 50% of the enzyme activity (PLA$_2$). It should be noted that CMT-10 was also found to inhibit human pancreatic PLA$_2$. A concentration of 30 μg/ml CMT-10 exhibited 66% inhibition.

These experimental results demonstrate a powerful new medical tool for preventing excessive PLA$_2$ activity and/or production which is believed to be responsible for the serious tissue destruction associated with many disease states and conditions.

Thus, while there has been described what are presently believed to be the preferred embodiments of the invention, those skilled in the art will understand that other and further modifications can be made without departing from the spirit of the invention. It is intended that the present invention includes all such modifications as come within the true scope of the invention as set forth in the claims.

What is claimed is:

1. A method for treating conditions associated with excess phospholipase A$_2$ activity and/or production in a mammal comprising administering to the mammal an amount of a non-antimicrobial tetracycline sufficient to inhibit said excess phospholipase A$_2$ activity and/or production;

wherein the excess phospholipase A$_2$ is present in the inflammatory process associated with sepsis, septic shock, pancreatitis, psoriasis, inflammatory bowel diseases or multisystem organ failure; and wherein the non-antimicrobial tetracycline is a dedimethylaminotetracycline.

2. The method of claim 1, wherein the dedimethylaminotetracycline is selected from the group consisting of 4-dedimethylaminotetracycline, 4-dedimethylamino- 5-oxytetracycline, 4-dedimethylamino-7-chlorotetracycline, 5a,6-anhydro-4-hydroxy-4-dedimethylaminotetracycline, 6-demethyl-6-deoxy-4-dedimethylaminotetracycline, 6α-deoxy-5-hydroxy-4-dedimethylaminotetracycline and 4-dedimethylamino-12a-deoxytetracycline and 4-dedimethylamino-11-hydroxy-12a-deoxytetracycline.

3. The method of claim 1, wherein the tetracycline is in a pharmaceutically acceptable carrier.

* * * * *